US011116403B2

(12) United States Patent
Shrubsole et al.

(10) Patent No.: US 11,116,403 B2
(45) Date of Patent: Sep. 14, 2021

(54) METHOD, APPARATUS AND SYSTEM FOR TAILORING AT LEAST ONE SUBSEQUENT COMMUNICATION TO A USER

(71) Applicant: KONINKLIJKE PHILIPS N.V., Eindhoven (NL)

(72) Inventors: Paul Anthony Shrubsole, Arnhem (NL); Murtaza Bulut, Eindhoven (NL); Christian Andreas Tiemann, Eindhoven (NL); Warner Rudolph Theophile Ten Kate, Waalre (NL); Chaitanya Dongre, Waals (NL)

(73) Assignee: Koninklijke Philips N.V., Eindhoven (NL)

( * ) Notice: Subject to any disclaimer, the term of this patent is extended or adjusted under 35 U.S.C. 154(b) by 136 days.

(21) Appl. No.: 16/323,542

(22) PCT Filed: Aug. 14, 2017

(86) PCT No.: PCT/EP2017/070535
§ 371 (c)(1),
(2) Date: Feb. 6, 2019

(87) PCT Pub. No.: WO2018/033498
PCT Pub. Date: Feb. 22, 2018

(65) Prior Publication Data
US 2019/0167105 A1    Jun. 6, 2019

(30) Foreign Application Priority Data
Aug. 16, 2016   (EP) .................................... 16184349

(51) Int. Cl.
*A61B 5/00*      (2006.01)
*G06Q 10/10*    (2012.01)
(Continued)

(52) U.S. Cl.
CPC ............ *A61B 5/0022* (2013.01); *A61B 5/165* (2013.01); *A61B 5/167* (2013.01); *G06Q 10/06* (2013.01);
(Continued)

(58) Field of Classification Search
CPC ....... A61B 5/0022; A61B 5/165; A61B 5/167; G16H 10/60; G16H 80/00
See application file for complete search history.

(56) References Cited

U.S. PATENT DOCUMENTS 6,401,085 B1 *  6/2002  Gershman .............. G16H 40/67
6,958,706 B2 * 10/2005  Chaco .................... G16H 80/00
                                                                    340/870.11
(Continued)

FOREIGN PATENT DOCUMENTS

WO    2014149133 A2    9/2014
WO    2014160549 A2    10/2014
(Continued)

OTHER PUBLICATIONS

Mishra, B. et al., "Facial expression recognition using feature based techniques and model based techniques: A survey", Electronics and Communication Systems (ICECS), 2015.
(Continued)

*Primary Examiner* — Michael Tomaszewski
*Assistant Examiner* — Jay M. Patel

(57) ABSTRACT

There is provided a method, apparatus and system for method for tailoring at least one subsequent communication to a user. Data acquired on the user in connection with a plurality of communications to the user is processed to determine a value for one or more characteristics indicative of a state of the user in connection with each communication. At least one communication parameter is varied in respect of each communication. The values for the one or
(Continued)

more characteristics indicative of the state of the user that are determined in connection with each communication are compared to identify one or more communication parameters that are most suitable for the user. One or more communication parameters are set for the at least one subsequent communication to the user according to the one or more identified communication parameters. The subsequent communication to the user is enabled based on the set one or more communication parameters.

16 Claims, 5 Drawing Sheets

(51) Int. Cl.
*G16H 10/60* (2018.01)
*G16H 80/00* (2018.01)
*G06Q 10/06* (2012.01)
*G06Q 50/22* (2018.01)
*A61B 5/16* (2006.01)

(52) U.S. Cl.
CPC ............ *G06Q 10/10* (2013.01); *G06Q 50/22* (2013.01); *G16H 10/60* (2018.01); *G16H 80/00* (2018.01)

(56) References Cited

U.S. PATENT DOCUMENTS

| | | |
|---|---|---|
| 2004/0147814 A1 | 7/2004 | Zancho et al. |
| 2008/0214903 A1* | 9/2008 | Orbach .................. G16H 10/65 600/301 |
| 2009/0259488 A1* | 10/2009 | Gounares ......... G06Q 10/06398 705/3 |
| 2010/0113072 A1* | 5/2010 | Gibson .................... H04W 4/12 455/466 |
| 2011/0071868 A1* | 3/2011 | Parker .................... G16H 80/00 705/2 |
| 2013/0339030 A1* | 12/2013 | Ehsani .................... G10L 17/00 704/275 |
| 2014/0142963 A1* | 5/2014 | Hill ......................... G16H 10/60 705/2 |
| 2015/0154492 A1* | 6/2015 | Ponomarev .............. G09B 5/04 706/11 |
| 2015/0173674 A1* | 6/2015 | Hayes .................. A61B 5/7278 600/301 |
| 2015/0213224 A1* | 7/2015 | Amarasingham ...... G16H 50/30 705/2 |
| 2017/0031449 A1* | 2/2017 | Karsten .................. G16H 50/20 |
| 2017/0041264 A1* | 2/2017 | Khomami Abadi ... G06Q 50/01 |

FOREIGN PATENT DOCUMENTS

| | | |
|---|---|---|
| WO | 2015091893 A1 | 6/2015 |
| WO | 2016110500 A1 | 7/2016 |

OTHER PUBLICATIONS

Malkovic, T., "Facial recognition app assesses patient pain", http://medicalxpress.com/news/2015-08-facial-recognition-app-patient-pain.html, 2015.

* cited by examiner

METHOD, APPARATUS AND SYSTEM FOR TAILORING AT LEAST ONE SUBSEQUENT COMMUNICATION TO A USER

CROSS-REFERENCE TO PRIOR APPLICATIONS

This application is the U.S. National Phase application under 35 U.S.C. § 371 of International Application No. PCT/EP2017/070535, filed on 14 Aug. 2017, which claims the benefit of U.S. Provisional Patent Application No. 16184349.5, filed on 16 Aug. 2016. These applications are hereby incorporated by reference herein.

TECHNICAL FIELD OF THE INVENTION

The invention relates to enabling, triggering, activating, managing or planning communications with a user and, in particular, relates to a method and apparatus for tailoring at least one communication to the user.

BACKGROUND TO THE INVENTION

The use of remote monitoring of users at home is becoming increasingly popular, particularly with the advances in the technology in this area. The remote monitoring of users is particularly beneficial in the case of unwell, unhealthy, or elderly users who live in their home environment, a retirement home, a nursing home, or otherwise outside a care facility. The systems that are used for remote monitoring are tailored to users that want to live independently, but also provide such users the reassurance that they are being supported to help maintain their health, safety and wellbeing.

Typically, as part of remote monitoring systems, remote interactions are provided between the user that is being monitored and another person (for example, a healthcare provider, a healthcare specialist, a care giver, a guardian, or any other person). Existing telephone and video conferencing solutions are sufficient for simple interactions and are relatively easy for the users to operate, at least in respect of answering call requests. As the technology for remote monitoring of users advances, the use of communications will become an integral part of this technology.

Currently, communications (such as video calls) are mainly provided through fixed hardware that is installed at the home of the user that is to be monitored. However, portable devices (such as laptops, tablet computers, and smart phones) are also becoming increasingly popular among users. Other options for providing communications also include smart watches and other wearable devices.

In the care industry, existing techniques for managing communications to users involve manual management and planning of communications at a remote facility. Such management and planning is generally realized by means of agenda(s), calendar(s), task manager solutions, which, regardless of their support (i.e. paper or electronic), require manual input and/or interaction by people at the remote facility (e.g. the caller). Specifically, people at the remote facility (e.g. callers) have to manually manage the planning for communications with their users (e.g. callees), and based on such planning, the communication is initiated to the user. Some users may need particular attention during certain times (for example, those users with depression, illness, pain, or mobility issues) and this is difficult to plan for when situations change. For example, to remotely address a noticeable change in the mental health of a user, a social situation or a physical health, a longer communication time is required compared to a regular communication to identify the problem and needs of the user. Consequently, this will affect the time that can be allocated to other users. When there are limited resources and many users (e.g. callees) then the aforementioned methods to solve such a dynamic scheduling system become challenging and prone to mistakes, which may be one of the cause of health deterioration of one or more users (e.g. the callees).

US 2011/0071868 A1 discloses a method for tailoring communications to a plurality of patients, which involves an analysis of the clinical priority of each communication, the likelihood of a patient responding to the communication if received at a particular time, and the available resources for performing the communications to prioritise and schedule the plurality of patient communications. However, the method only uses static information in prioritising and scheduling communications, which means that the priority and schedule that is set is not always optimum for a user in a current situation. For example, the prioritisation may not be reliable since some users may require more frequent (or urgent) communication due to a changing situation and the scheduling may not be convenient for users in view of the current situation.

Therefore, there is a need for an improved method and monitoring apparatus for tailoring communication between a first person (for example, a healthcare provider, a healthcare specialist, a care giver, a guardian, or any other person) and a second person (e.g. a patient, a user, a subject) who is remotely monitored by the first person.

SUMMARY OF THE INVENTION

As noted above, one of the limitations with existing techniques for managing communications with remotely monitored users is that the prioritisation and scheduling of communications is not always optimum for users, therefore deterioration of the users' (health) conditions may not be detected/assessed in time.

Therefore, according to a first aspect of the invention, there is provided a method for tailoring at least one subsequent communication to a user. The method comprises processing, by a logic, data acquired on the user in connection with a plurality of communications to the user to determine a value for one or more characteristics indicative of a state of the user in connection with each communication, wherein at least one communication parameter is varied in respect of each communication. The method also comprises comparing, by the logic, the values for the one or more characteristics indicative of the state of the user that are determined in connection with each communication to identify one or more communication parameters that are most suitable for the user. The method further comprises the steps of setting, by the logic, one or more communication parameters for the at least one subsequent communication to the user according to the one or more identified communication parameters. The method further comprise the step of enabling, by the logic, the at least one subsequent communication to the user based on the set one or more communication parameters.

In some embodiments, a plurality of communication parameters may be varied in respect of each communication and the plurality of communication parameters may be varied simultaneously or in a predefined order.

In some embodiments, the data acquired on the user may comprise any one or more of: physiological data, psychological data, audio data, visual data, and user input data.

In some embodiments, the enabling of the at least one subsequent communication may comprise sending an alert, a notification an alarm such that a person initiate the subsequent communication to the user. Additionally or alternatively, such may comprise activating, performing, triggering, starting or otherwise initiating a communication device to initiate the subsequent communication to the user.

In some embodiments, the method may further comprise acquiring contextual information in connection with each communication and weighting the determined values for the one or more characteristics indicative of a state of the user based on the acquired contextual information.

In some embodiments, the contextual information may be acquired from at least one sensor in an environment of the user.

In some embodiments, the method may further comprise detecting a deviation in at least one characteristic indicative of the state of the user and, when the deviation is detected, acquiring contextual information from the user.

In some embodiments, the method may further comprise updating the one or more communication parameters set for the at least one subsequent communication based on any one or more of: an identified current activity of the user, an identified activity pattern of the user, a deviation from an identified activity pattern of the user, and an input received from the user indicative of a current state of the user.

In some embodiments, the at least one communication parameter may comprise any one or more of: a time for the communication to the user, a duration of the communication to the user, a content for the communication to the user, an affective level for the content of the communication to the user, a difficulty level for the content of the communication to the user, a cognitive level for the content of the communication to the user, and a form of the communication to the user.

In some embodiments, the one or more characteristics indicative of a state of the user may comprise any one or more of: a characteristic indicative of an affective state of the user, a characteristic indicative of a mobility capability of the user, a characteristic indicative of a level of pain experienced by the user, a characteristic indicative of a physiological state of the user, a characteristic indicative of a psychological state of the user, a characteristic indicate of a strength of the user, a characteristic indicative of an impairment of the user, a characteristic indicative of a cognitive ability of the user, and a characteristic indicative of a level of social skills of the user.

In some embodiments, the method may further comprise performing the method for a plurality of users and assigning a priority value to at least one of the plurality of users, wherein setting one or more communication parameters for at least one subsequent communication may take into account the priority value assigned to the at least one of the plurality of users.

In some embodiments, the method may further comprise detecting a deviation in at least one characteristic indicative of the state of the user and repeating the method of the first aspect of the invention to re-set one or more communication parameters for at least one subsequent communication to the user.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to a third aspect of the invention, there is provided an apparatus for tailoring at least one communication to a user, the apparatus comprising a control unit. The control unit is configured to process data acquired on the user in connection with a plurality of communications to the user to determine a value for one or more characteristics indicative of a state of the user in connection with each communication, wherein at least one communication parameter is varied in respect of each communication. The control unit is also configured to compare the values for the one or more characteristics indicative of a state of the user that are determined in connection with each communication to identify one or more communication parameters that are most suitable for the user and set one or more communication parameters for at least one subsequent communication to the user according to the one or more identified communication parameters. The control unit is further configure to enable the at least one subsequent communication to the user based on the set one or more communication parameters.

In some embodiments, the apparatus may further comprise a memory configured to store the values for the one or more characteristics indicative of a state of the user that are determined in connection with the communications and the associated communication parameters for the communications.

In some embodiments, the control unit may be configured to acquire contextual information in connection with the plurality of communications from at least one sensor in an environment of the user.

According to the aspects and embodiments described above, the limitations of existing techniques are addressed. The most appropriate settings for the user can be selected automatically and the subsequent communication can be triggered, initiated, activated or otherwise enabled based on said appropriate setting, thereby ensuring effective and adequate remote monitoring of users. According to the above aspects and embodiments, a self-calibrating system is provided that analyses characteristics indicative of the state of the user to determine the most appropriate or optimal communication parameters for subsequent communication, by with the needs of users are tailored, optimized, or otherwise adapted to their (health) conditions. Also, in a multi-user situation, communications can be prioritised and scheduled optimally across multiple users, thereby ensuring that each user of the multiple users receives the appropriate remote monitoring communication based on their (health) conditions. In other words, the aspects and embodiments described above provide for means to increase the health quality of user by limiting the chance of degradation of said users' (health) conditions by tailored, optimal or otherwise adapted remote monitoring thereof.

According to a fourth aspect of the invention, there is provided a system for tailoring at least one communication to a user, the system comprising one or more sensors and a control unit. The one or more sensors are configured to for acquiring data on the user in connection with a plurality of communications, wherein one data comprise or more of: physiological data, psychological data, audio data, visual data, and user input. As it will be further elucidated hereunder, the one or one sensors may be any type of sensor that can acquire data on the user. The control unit is configured to process data acquired on the user in connection with a plurality of communications to the user to determine a value for one or more characteristics indicative of a state of the user in connection with each communication, wherein at least one communication parameter is varied in respect of each communication. The control unit is also configured to compare the values for the one or more characteristics indicative of a state of the user that are determined in connection with each communication to identify one or more communication parameters that are most suitable for the user and set one or more communication parameters for at least one subsequent communication to the user according to the one or more identified communication parameters. The control unit is also configure to enable the at least one subsequent communication to the user based on the set one or more communication parameters.

There is thus provided an improved method and method and monitoring apparatus for enabling communication between a first person (for example, a healthcare provider, a healthcare specialist, a care giver, a guardian, or any other person) and a second person who is remotely monitored by the first person (e.g. a patient, a user, a subject).

In an example, there is provided method for setting one or more communication parameters for at least one communication to a user. The method comprises processing data acquired on the user in connection with a plurality of communications to the user to determine a value for one or more characteristics indicative of a state of the user in connection with each communication, wherein at least one communication parameter is varied in respect of each communication. The method also comprises comparing the values for the one or more characteristics indicative of the state of the user that are determined in connection with each communication to identify one or more communication parameters that are most suitable for the user and setting one or more communication parameters for at least one subsequent communication to the user according to the one or more identified communication parameters.

In a further example, there is provided a computer program product comprising a computer readable medium, the computer readable medium having computer readable code embodied therein, the computer readable code being configured such that, on execution by a suitable computer or processor, the computer or processor is caused to perform the method or the methods described in the above paragraph.

In a further example, there is provided an apparatus for setting one or more communication parameters for at least one communication to a user, the apparatus comprising a control unit. The control unit is configured to process data acquired on the user in connection with a plurality of communications to the user to determine a value for one or more characteristics indicative of a state of the user in connection with each communication, wherein at least one communication parameter is varied in respect of each communication. The control unit is also configured to compare the values for the one or more characteristics indicative of a state of the user that are determined in connection with each communication to identify one or more communication parameters that are most suitable for the user and set one or more communication parameters for at least one subsequent communication to the user according to the one or more identified communication parameters.

In a further example, there is provided a system for setting one or more communication parameters for at least one communication to a user, the apparatus comprising a control unit, the system comprising one or more sensors and a control unit. The one or more sensors are configured to for acquiring data on the user in connection with a plurality of communications, wherein one data comprise or more of: physiological data, psychological data, audio data, visual data, and user input. As it will be further elucidated hereunder, the one or one sensors may be any type of sensor that can acquire data on the user. The control unit is configured to process data acquired on the user in connection with a plurality of communications to the user to determine a value for one or more characteristics indicative of a state of the user in connection with each communication, wherein at least one communication parameter is varied in respect of each communication. The control unit is also configured to compare the values for the one or more characteristics indicative of a state of the user that are determined in connection with each communication to identify one or more communication parameters that are most suitable for the user and set one or more communication parameters for at least one subsequent communication to the user according to the one or more identified communication parameters.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

Figure 1:
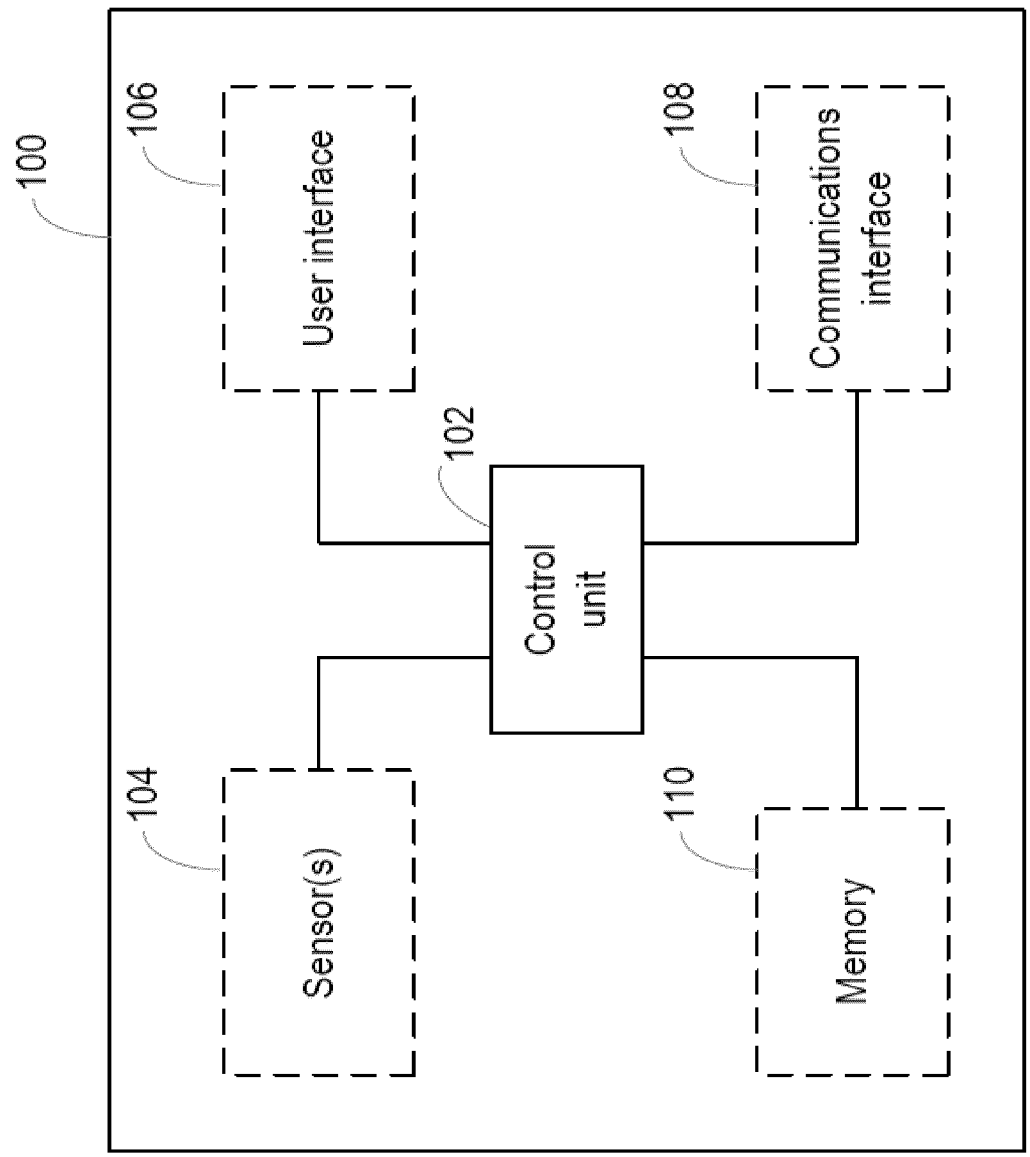
FIG. 1 is a block diagram of an apparatus according to an embodiment.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 shows a block diagram of an apparatus 100 according to an embodiment of the invention that can be used for setting one or more communication parameters for at least one communication to a user.

The apparatus 100 comprises a control unit 102 ((also referred to generally as "logic") that controls the operation of the apparatus 100 and that can implement the method described herein. The control unit 102 can comprise one or more processors, processing units, multi-core processors or modules that are configured or programmed to control the apparatus 100 in the manner described herein. In particular implementations, the control unit 102 can comprise a plurality of software and/or hardware modules that are each configured to perform, or are for performing, individual or multiple steps of the method according to embodiments of the invention.

Briefly, the control unit 102 is configured to process data acquired on the user in connection with a plurality of communications to the user to determine a value for one or more characteristics indicative of a state of the user in connection with each communication, wherein at least one communication parameter is varied in respect of each communication. A communication can comprise an audio call, a video call, an audio and video call, an e-mail, or any other form of communication or combination of forms of communication. The data acquired on the user may comprise any one or more of physiological data, psychological data, audio data, visual data, user input data, contextual data (such as environmental sensor data), or any other data on the user or combination of data on the user.

In some embodiments, the control unit 102 is configured to control one or more sensors 104 to acquire the data. In the illustrated embodiment of FIG. 1, the apparatus 100 comprises one or more sensors 104. However, it will be understood that one or more sensors may alternatively or additionally be external to (i.e. separate to or remote from) the apparatus 100. In some embodiments, a wearable device can comprise one or more sensors. In these embodiments, the one or more sensors of the wearable device can acquire data on the user wearing the wearable device. A wearable device may be in the form of a watch, a necklace, a patch, a band for a part of the body, or any other device designed to be worn by a user. In some embodiments, a mobile device (such as a smartphone, a tablet, a laptop computer, or any other mobile device) can comprise one or more sensors. In some embodiments, the apparatus 100 may itself be a mobile device. In some embodiments, one or more sensors may be designed to be placed in the environment of the user. For example, a sensor may be wall-mountable sensor.

Control unit 102 may take various forms, such as one or more computing devices contained within and/or outside of a communication device that is configured to perform selected aspects of the present disclosure. In some embodiments, control unit 102 may take the form of an application-specific integrated circuit ("ASIC") or a field-programmable gate array ("FPGA"). In other embodiments, control unit 102 may include one or more processors and memory storing instructions that cause the one or more processors to perform selected aspects of the present disclosure. In various embodiments, the sensors may be communicatively coupled with control unit 102 and/or each other via one or more wired or wireless communication networks (not depicted) that employ various types of communication technologies, such as Wi-Fi, ZigBee, Z-wave, Bluetooth, Ethernet, etc.

A sensor may be any type of sensor that can acquire data on the user. For example, a sensor can be a physiological or vital signs sensor (such as a heart rate sensor, a blood pressure sensor, a skin conductivity sensor, a muscle activity sensor, a skin temperature sensor, a respiration rate sensor, or any other physiological sensor), an audio sensor that can acquire audio data on the user (such as a microphone or any other audio sensor), a visual sensor that can acquire visual data on the user (such as a camera, a video, an infra-red sensor, or any other visual sensor or combination of visual sensors), an activity or motion sensor (such as an accelerometer, a gyroscope, a magnetometer, a visual sensor, a pressure sensor, or any other inertial, activity or motion sensor), a location sensor, a calorie intake sensor, an open/close sensor (for example, to detect usage of doors or cupboards), or an environment sensor (such as a sensor configured to sense a time of day, a light sensor, an ambient temperature sensor, a $CO_2$ level sensor, a humidity sensor, or a noise level sensor). Although examples have been provided for the type of sensor that can acquire data on the user, it will be understood that any sensor suitable to acquire data on the user or any combination of sensors suitable to acquire data on the user can be used.

A physiological (or vital signs) sensor may be any sensor suitable to acquire physiological data on the user. For example, a physiological sensor can comprise one or more of a heart rate sensor (such as an electrocardiogram ECG sensor, a photoplethysmography PPG sensor, a phonocardiography PCG sensor, or any other heart rate sensor), a vibration detection sensor or an audio physiological sensor for acquiring (such as such as microphone, a capacitive micromachined ultrasonic transducer CMUT sensor, an accelerometer, a strain gauge, a responsive material, or any other acoustic physiological sensor), a skin conductivity sensor, a muscle activity sensor (such as an electromyography EMG sensor), a temperature sensor (such as a skin temperature sensor), a respiratory rate sensor, a blood oxygenation (SpO2) sensor, a brain activity sensor (such as an electroencephalogram EEG sensor), or any other type of physiological sensor or combination of physiological sensors suitable to acquire physiological data on the user. A physiological sensor can acquire physiological data indicative of a state of the user. For example, a change in the heart rate, skin conductivity, blood pressure, respiration rate, skin temperature, or the like can indicate that the user is in a negative mental or physical state (for example, stressed, uncomfortable, in pain, upset or similar). In some embodiments, one or more physiological sensors may be integrated into a wearable device. In these embodiments, a physiological sensor can acquire physiological data on the user wearing the wearable device.

A visual sensor may be any sensor suitable to acquire visual data on the user. For example, a visual sensor can comprise one or more of a camera, a video, an infrared sensor, or any other visual sensor or combination of visual sensors. A visual sensor may be designed to be placed in the environment of the user (for example, at the home of the user, at a healthcare facility, or similar). The visual sensor may acquire visual data indicative of a state of the user (for example, data indicative of facial expressions, posture, movement, physiological characteristics such as heart rate, respiration rate, respiration depth, exhalation time, inhalation time, SpO2 level, or any other physiological characteristics, or any other visual data indicative of a state of the user). The control unit 102 may be configured to recognise predefined facial expressions, postures and/or movements in visual data to determine a value for one or more characteristics indicative of a state of the user. Similarly, the control unit 102 may be configured to recognise predefined motion in visual data specific to an activity to determine a value for one or more characteristics indicative of a state of the user. The control unit 102 may be configured to recognise a gesture or action from the user to determine a value for one or more characteristics indicative of a state of the user in connection with each communication. In some embodiments, the visual sensor may also acquire data indicative of the state of the environment. The data indicative of the state of the environment can be used in determining the state of the user.

An audio sensor may be any sensor suitable to acquire audio data on the user. For example, an audio sensor can comprise a microphone or any other acoustic sensor or combination of audio sensors. An audio sensor may be designed to be placed in the environment of the user (for example, at the home of the user, at a healthcare facility, or similar). The audio sensor may acquire audio data indicative of a state of the user. For example, the control unit 102 may be configured to recognise tones of voice, language, trigger words, or predefined sounds (such as a user crying, groaning, laughing, or similar) in acoustic data to determine a value for one or more characteristics indicative of a state of the user. Similarly, the control unit 102 may be configured to recognise sounds specific to an activity to determine a value for one or more characteristics indicative of a state of the user. The control unit 102 may be configured to recognise a vocal instruction from the user to determine a value for one or more characteristics indicative of a state of the user. In some embodiments, the audio sensor may also acquire data indicative of the state of the environment. As previously mentioned, the data indicative of the state of the environment can be used in determining the state of the user.

An activity or motion sensor may be any sensor suitable to acquire activity or motion data on the user. For example, an activity or motion sensor can comprise one or more of an accelerometer, a gyroscope, a magnetometer, a visual sensor, an air pressure sensor, a passive infrared (PIR) sensor, an open/close sensor, a pressure mat sensor, power sensors, or any other activity or motion sensor, or combination of activity or motion sensors. In some embodiments, one or more activity or motion sensors may be integrated into a wearable device. In these embodiments, the sensor can acquire data indicative of any activity or motion of a user wearing the wearable device. In some embodiments, an activity or motion sensor may be a sensor designed to be placed in the environment of the user (for example, at the home of the user, at a healthcare facility, or similar). In these embodiments, the sensor can acquire data indicative of any activity or motion in the environment in which the sensor is placed. A certain activity or motion can be used to determine a value for one or more characteristics indicative of a state of the user.

An environment sensor is a sensor designed to be placed in the environment of the user. An environment sensor may be any sensor that can acquire contextual information (or data) suitable to put the one or more characteristics indicative of a state of the user into context. For example, an environment sensor can comprise one or more of a sensor configured to sense a time of day, a light sensor, an ambient temperature sensor, a $CO_2$ level sensor, a humidity sensor, a noise level sensor, a visual sensor, an audio sensor or any other environment sensor suitable to acquire contextual information suitable to put the one or more characteristics indicative of a state of the user into context.

Although some examples have been provided above for sensors, their arrangement, and operation, those skilled in the art will be aware of other types of sensor that can be used to acquire data on the user and other arrangements and operations for the sensors. In some embodiments, multiple types of sensor and arrangements of sensors can be used. In some embodiments, in addition or as an alternative to the control unit 102 being configured to control one or more sensors 104 to acquire data on the user, the control unit 102 may be configured or further configured to acquire data on the user from one or more user interfaces 106, which will be explained in more detail later.

As mentioned previously, the control unit 102 is configured to determine a value for one or more characteristics indicative of a state of the user in connection with each communication by processing the data acquired on the user. The one or more characteristics indicative of the state of the user may comprise any one or more of a characteristic indicative of an affective (for example, emotional) state of the user, a characteristic indicative of a mobility capability of the user, a characteristic indicative of a level of pain experienced by the user, a characteristic indicative of a physiological state of the user, a characteristic indicative of a psychological state of the user, a characteristic indicate of a strength of the user, a characteristic indicative of an impairment of the user, a characteristic indicative of a cognitive ability of the user, a characteristic indicative of a level of social skills of the user (for example, the communication ability of the user such as their speaking ability, their hearing ability, or the like), or any other characteristics indicative of a state of the user, or any combination of characteristics indicative of a state of the user.

The at least one communication parameter that is varied in respect of each communication may comprise any one or more of a time for the communication to the user, a duration of the communication to the user, a content for the communication to the user, an affective (for example, emotional) level for the content of the communication to the user, a difficulty level for the content of the communication to the user, a cognitive level for the content of the communication to the user, a form of the communication to the user, or any other communication parameter or combination of communication parameters.

The control unit 102 is also configured to compare the values for the one or more characteristics indicative of a state of the user that are determined in connection with each communication to identify one or more communication parameters that are most suitable for the user (for example, optimal for the user). The control unit 102 is further configured to set one or more communication parameters for at least one subsequent communication to the user according to the one or more identified communication parameters.

In some embodiments, the control unit 102 of the apparatus 100 may also be configured to acquire contextual information in connection with the plurality of communications from at least one sensor in an environment of the user. The contextual information may be any information suitable to put the one or more characteristics indicative of a state of the user into context.

According to some embodiments, the apparatus 100 may also comprise at least one user interface 106. Alternatively or in addition, a user interface 106 may be external to (i.e. separate to or remote from) the apparatus 100. For example, the user interface 106 may be part of another device.

A user interface 106 may be for use in providing the user of the apparatus 100 with information resulting from the method according to the invention. The control unit 102 may be configured to control one or more user interfaces 106 to provide information resulting from the method according to the invention. For example, the control unit 102 may be configured to control one or more user interfaces 106 to render the one or more communication parameters that are set for the at least one subsequent communication or any other information determined by the methods described herein. In some embodiments, the user interface 106 may be operable to render a prompt to a person to ask certain questions during a communication to the user (for example, if certain characteristics indicative of the state of the user are detected).

Alternatively or in addition, a user interface 106 may be configured to receive a user input. In other words, a user interface 106 may allow the user of the apparatus 100 to manually enter data, instructions, or information. For example, in some embodiments, a user interface 106 may be operable to receive a user input comprising data on the user in connection with the plurality of communications to the user, which the control unit 102 can acquire and process in the determination of a value for one or more characteristics indicative of a state of the user in connection with each communication. In some embodiments, a user input may be an annotation (for example, a label) to include with a communication, which may improve learning.

As mentioned earlier, in some embodiments, in addition or as an alternative to the control unit 102 being configured to control one or more sensors 104 to acquire data on the user, the control unit 102 may be configured or further configured to acquire data on the user from one or more user interfaces 106. In other words, in some embodiments, one or more user interfaces 106 may receive data on the user. For example, one or more user interfaces 106 may be for use in providing the user with a questionnaire or a prompt to describe their state. In one embodiment, the one or more user interfaces 106 may receive the data verbally from the user. In such an embodiment, the control unit 102 may then use speech recognition and natural language processing to determine the state of the user. In another embodiment, the one or more user interfaces 106 may receive the data in text format from the user. In such an embodiment, the control unit 102 may then use natural language processing to determine the state of the user. The data on the user acquired from one or more user interfaces 106 may be particularly useful where data acquired from the sensors 104 is inconsistent (for example, pointing to different user states).

A user interface 106 may be or may comprise any component that enables rendering or output of information, data or signals to the user of the apparatus 100. Alternatively or in addition, a user interface 106 may be or may comprise any component that enables the user of the apparatus 100 to provide a user input, interact with and/or control the apparatus 100. For example, the user interface 106 may comprise one or more switches, one or more buttons, a keypad, a keyboard, a touch screen or an application (for example, on a tablet or smartphone), a display screen or other visual indicator, one or more speakers, one or more microphones, any other voice dialogue components, one or more lights, a component for providing tactile feedback (for example, a vibration function), or any other user input, or combination of user interfaces.

In some embodiments, the apparatus 100 may also comprise a communications interface 108 for enabling the apparatus 100 to communicate with any components, interfaces, units, sensors and devices that are internal or external to the apparatus 100. The communications interface 108 may communicate with any components, interfaces units, sensors and devices wirelessly or via a wired connection. For example, in the embodiments where one or more user interfaces 106 are external to the apparatus 100, the communications interface 108 may communicate with any external user interfaces wirelessly or via a wired connection. Similarly, in the embodiments where the one or more sensors 104 are external to the apparatus 100, the communications interface 108 may communicate with the any external sensors wirelessly or via a wired connection.

In some embodiments, the apparatus 100 may also comprise a memory 110 configured to store program code that can be executed by the control unit 102 to perform the method described herein. The memory 110 can also be used to store information, data, signals and measurements made or acquired by the control unit 102 of the apparatus 100 or by components, interfaces, units, sensors and devices that are external to the apparatus 100. For example, the memory 110 may be configured to store one or more of the values for the one or more characteristics indicative of a state of the user that are determined in connection with the communications, the associated communication parameters for the communications, any contextual information that is acquired, the one or more communication parameters that are set for the at least one subsequent communication, any annotations (or labels) for a communication, and/or any other data made or acquired by the control unit 102. The control unit 102 may be configured to control the memory 110 to store the data.

It will be appreciated that FIG. 1 only shows the components required to illustrate this aspect of the invention, and in a practical implementation, the apparatus 100 may comprise additional components to those shown. For example, the apparatus 100 may comprise a battery or other power supply for powering the apparatus 100 or means for connecting the apparatus 100 to a mains power supply.

Figure 2A:
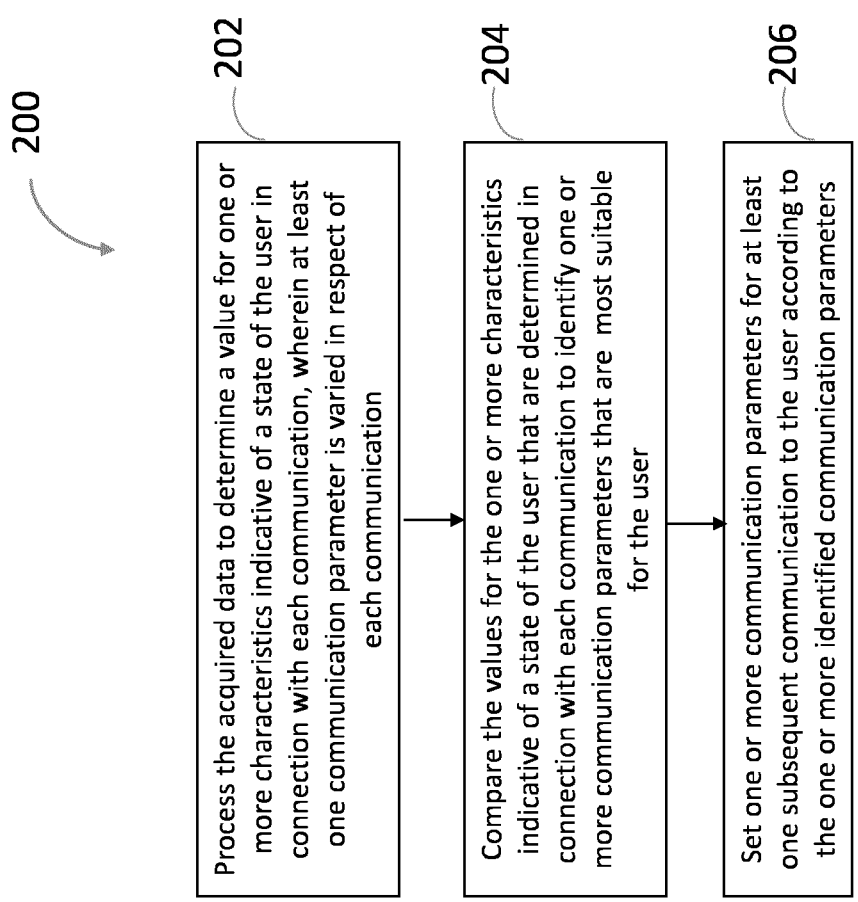
FIG. 2A is a flow chart illustrating a method according to an embodiment.

FIG. 2A illustrates a method 200 for setting one or more communication parameters for at least one communication to a user according to an embodiment. The illustrated method 200 can generally be performed by or under the control of the control unit 102 of the apparatus 100.

With reference to FIG. 2A, at block 202, data acquired on the user in connection with a plurality of communications to the user is processed to determine a value for one or more characteristics indicative of a state of the user in connection with each communication. As mentioned earlier, a communication can comprise an audio call, a video call, an audio and video call, an e-mail, or any other form of communication or combination of forms of communication. As also mentioned earlier, the data acquired on the user may comprise any one or more of physiological data, psychological data, audio data, visual data, user input data, or any other data on the user or combination of data on the user. The data acquired on the user in connection with a plurality of communications to the user may comprise data that is acquired on the user during a communication and, alternatively or in addition, data that is acquired on the user around the communication. For example, in some embodiments, data on the user may be acquired continuously (such as throughout the day) or at certain times of the day.

In respect of each of the plurality of communications, at least one communication parameter is varied (for example, set differently). In this way, it is possible to randomise controllable aspects of the communications to determine the most suitable (or optimal) communication parameters for at least one subsequent communication. For example, a first communication may be at first time of day, whereas a second communication may be at a second time of day, which is different to the first time of day. It can then be determined which of the first or second time of day is the most suitable (or optimal) time of day for the user to receive a communication. For example, it may be determined from the body language of the user and the tone of the user at the time of the first and second communications that the user is more alert or cheerful in the mornings. Thus, in this way, a self-calibration can be performed by varying communication parameters to determine the sensitivity or invariance of the user to those communication parameters to select the optimal communication parameters for at least one subsequent communication. In some embodiments, it may be that the randomness of varying the at least one communication parameter is never set to zero. This allows for the detection of unexpected user patterns. In this way, the chance of gathering new information about the user that can be used in setting communication parameters can be increased.

In some embodiments, the randomness of the plurality of communications to the user may be adjusted based on the values for the one or more characteristics indicative of a state of the user that are determined in connection with each communication. For example, the frequency of the plurality of communications to the user may be adjusted in this way. At the start of implementing the method, there may be little or no prior information available and thus the randomness in the variable communications parameters may be greater. Later, depending on the response of the user to the communications (i.e. based on the values for the one or more characteristics indicative of a state of the user that are determined in connection with each communication), the randomness in the variable communications parameters can be decreased. In other words, more user-specific settings can be selected. For example, a user may express discomfort from the random nature of the initial plurality of communications to the user. In this case, the calibration time may be extended to take this factor into account (e.g., a default calibration time of 1 week may be increased to 3 weeks).

In some embodiments, more than one (i.e. a plurality of) communication parameters are varied in respect of each communication. In these embodiments, the plurality of communication parameters may be varied simultaneously or may be varied in a predefined order. The predefined order may be selected (or adjusted or adapted) based on information associated with the user. For example, the information can comprise any one or more of a profile of the user (which may comprise information on one or more languages for the user, a culture for the user, or any other information on the user), a medical condition of (or disease affecting) the user, an existing schedule for the user, data collected during previous communications to the user, or any other information or combination of information associated with the user.

In this way, the communication parameters can be calibrated in a different order that fits to the information associated with the user. For example, for a user with an irregular schedule, the timing of the communication can be calibrated first, while for a user with cognitive decline the difficulty level of the questions can be calibrated first. Where the information associated with the user changes (for example, through one or more of an update to a user profile, a change in a medical condition or disease, a change in an existing schedule, or similar), communication parameters may be removed and, alternatively or in addition, other communication parameters may be included. Alternatively or in addition, the order in which the communication parameters are varied may be adjusted based on a change in the information associated with the user.

In some embodiments, at least one of the plurality of communications to the user may be an attempted communication that is unsuccessful. In other words, a communication can be initiated but the connection to the user may fail. For example, the user may not be available or able to receive a communication.

Thus, at block 202, data acquired on the user in connection with a plurality of communications to the user is processed to determine a value for one or more characteristics indicative of a state of the user in connection with each communication. For example, dominant features or characteristics indicative of the state of the user are extracted and scored. As mentioned previously, the one or more characteristics indicative of the state of the user may comprise any one or more of a characteristic indicative of an affective (for example, emotional) state of the user, a characteristic indicative of a mobility capability of the user, a characteristic indicative of a level of pain experienced by the user, a characteristic indicative of a physiological state of the user, a characteristic indicative of a psychological state of the user, a characteristic indicate of a strength of the user, a characteristic indicative of an impairment of the user, a characteristic indicative of a cognitive ability of the user, a characteristic indicative of a level of social skills of the user (for example, the communication ability of the user such as their speaking ability, their hearing ability, or the like), or any other characteristics indicative of a state of the user, or any combination of characteristics indicative of a state of the user.

By analysing certain characteristics of the user in connection with a plurality of calls, it is possible to infer the state of the user. The one or more characteristics indicative of the state of the user may be identified from the data acquired on the user using any known method for identifying the particular characteristic. For example, a method for identifying a characteristic indicative of the state of the user may comprise an emotion detection method, a pain detection method, a mobility detection method, or the like. The data acquired on the user in connection with the plurality of communications can be processed using such a method. In some embodiments, the processing of data may involve a comparison of the data with models (such as models of the human anatomy, behaviour, or the like) to identify characteristics indicative of the state of the user. The models may comprise data acquired from the user in the past (for example, historical data for the user).

In one embodiment, a pain detection method can be used to analyse video and audio data acquired from the user. For example, the analysis can involve the detection of characteristics such as changes around the eyes of the user, in the tone of voice of the user, in the posture of the user (for example, whether the user is leaning back, leaning forward, stable, unstable, restless, or the like), or similar, when compared to previously observed characteristics.

In another embodiment, an emotion and pain detection method can be used to analyse audio (for example, speech) data acquired from the user. For example, speech data may be collected during the regular check-up calls. In such an embodiment, the value for one or more characteristics indicative of an emotional, mood and pain state of the user in connection with each communication may be determined. For example, one or more characteristics indicative of an emotional state or mood of the user may be detected using a facial expression recognition technique. In some embodiments, a plurality of different facial expressions may be analysed. The analysis may be in real-time. Similarly, a facial expression recognition technique may be used to detect one or more characteristics indicative of a level of pain experienced by the user.

In another embodiment, a mobility detection method can be used to analyse video data acquired from the user. For example, the video data may be acquired using a camera with a field of view set to determine the difference in movement of the body of the user compared to similar movements made in the past.

In another embodiment, physiological data acquired from the user may be analysed. For example, analysis of one or more of an acquired skin conductivity of the user, an acquired heart rate of the user, a determined heart rate variability of the user, or other physiological data or combination thereof can be used to determine the mood, anxiety level, or stress level of the user. In another example, the tiredness of the user may be determined through one or more of speech analysis on audio data, facial expression analysis on visual data and body posture analysis.

In another embodiment, psychological data acquired on the user may be analysed. For example, depression of the user may be detected from a speech analysis performed on acquired audio data (such as observing long term changes in speech). In another example, the anxiety level of the user may be estimated by determining a variability in an acquired heart rate of the user over a period of time (for example, during a communication). In another example, a cognitive level for the user may be determined through speech analysis on audio data.

Although examples have been provided for ways in which certain characteristics of the user may be analysed to determine the state of the user, it will be understood that other analysis methods may be used and other states of the user may be determined.

The one or more characteristics may each be converted into a value (or score) indicative of the state of the user in connection with each communication. The value can be an integer value (for example, an integer value between 1 and 10, or any other integer value). The value may be indicative of a level of concern in relation to the state of the user. For example, a higher value may indicate a higher level of concern in relation to the state of the user. In an example, the values for a plurality of characteristics indicative of the state of the user in connection with a communication may be: Emotion 5, Mobility 5, Pain 7. Although an example has been provided for the characteristics and values for those characteristics, it will be understood that other characteristics and values are also possible.

As mentioned earlier, the at least one communication parameter may comprise any one or more of: a time for the communication to the user, a duration of the communication to the user, a content for the communication to the user, an affective (for example, emotional) level for the content of the communication to the user, a difficulty level for the content of the communication to the user, a cognitive level for the content of the communication to the user, a form of the communication to the user, or any other communication parameter or combination of communication parameters.

Returning to FIG. 2A, at block 204, the values for the one or more characteristics indicative of the state of the user that are determined in connection with each communication are compared to identify one or more communication parameters that are most suitable for the user. In other words, the respective values of the one or more characteristics in connection with each communication are compared such that the relative change (or difference) in respective values can be determined. In this way, one or more communication parameters that are optimal for (or fitting to, suitable for, appropriate for, or compatible with) the state of the user can be identified. Specifically, the difference in respective values across the communications can be used as an input to set communication parameters for subsequent communications (at block 206).

As mentioned earlier, the one or more characteristics indicative of the state of the user may comprise any one or more of a characteristic indicative of an affective (for example, emotional) state of the user, a characteristic indicative of a mobility capability of the user, a characteristic indicative of a level of pain experienced by the user, a characteristic indicative of a physiological state of the user, a characteristic indicative of a psychological state of the user, a characteristic indicate of a strength of the user, a characteristic indicative of an impairment of the user, a characteristic indicative of a cognitive ability of the user, a characteristic indicative of a level of social skills of the user (for example, the communication ability of the user such as their speaking ability, their hearing ability, or the like), or any other characteristics indicative of a state of the user, or any combination of characteristics indicative of a state of the user. In general, the one or more characteristics indicative of the state of the user may be a combination of objective information (such as that measured by sensors) and subjective information (such as that perceived by the user or another person).

At block 206 of FIG. 2A, one or more communication parameters are set for at least one subsequent communication to the user according to the one or more identified communication parameters. The one or more communication parameters that are set for at least one subsequent communication may comprise any one or more of a time for the communication to the user, a duration of the communication to the user, a content for the communication to the user, an affective (for example, emotional) level for the content of the communication to the user, a difficulty level for the content of the communication to the user, a cognitive level for the content of the communication to the user, a form of the communication to the user (for example, the form of the communication may be changed from one form of communication to another form of communication), or any other communication parameter or combination of communication parameters. In some embodiments, the communication parameter set for at least one subsequent communication can include assignment of a person to perform the at least one subsequent communication. For example, the reaction of the user to different people performing the plurality of communications may be analysed to find the best match of person for the user to perform the at least one subsequent communication (which may depend on the availability of the person to perform the at least one subsequent communication).

Although not illustrated in FIG. 2A, in some embodiments, the method may further comprise updating the one or more communication parameters set for the at least one subsequent communication based on any one or more of an identified current activity of the user (for example, sleeping, toileting, eating, bathing, out of house, having visitors, or any other activity in which the user is engaging), an identified activity pattern of the user, a deviation from an identified activity pattern of the user, an input received from the user indicative of a current state of the user, or similar. For example, the one or more communication parameters set for at least one subsequent communication may be updated based on historical information (such as the identified activity pattern of the user) derived from trend analysis together with real-time data (such as the identified current activity of the user).

Figure 2B:
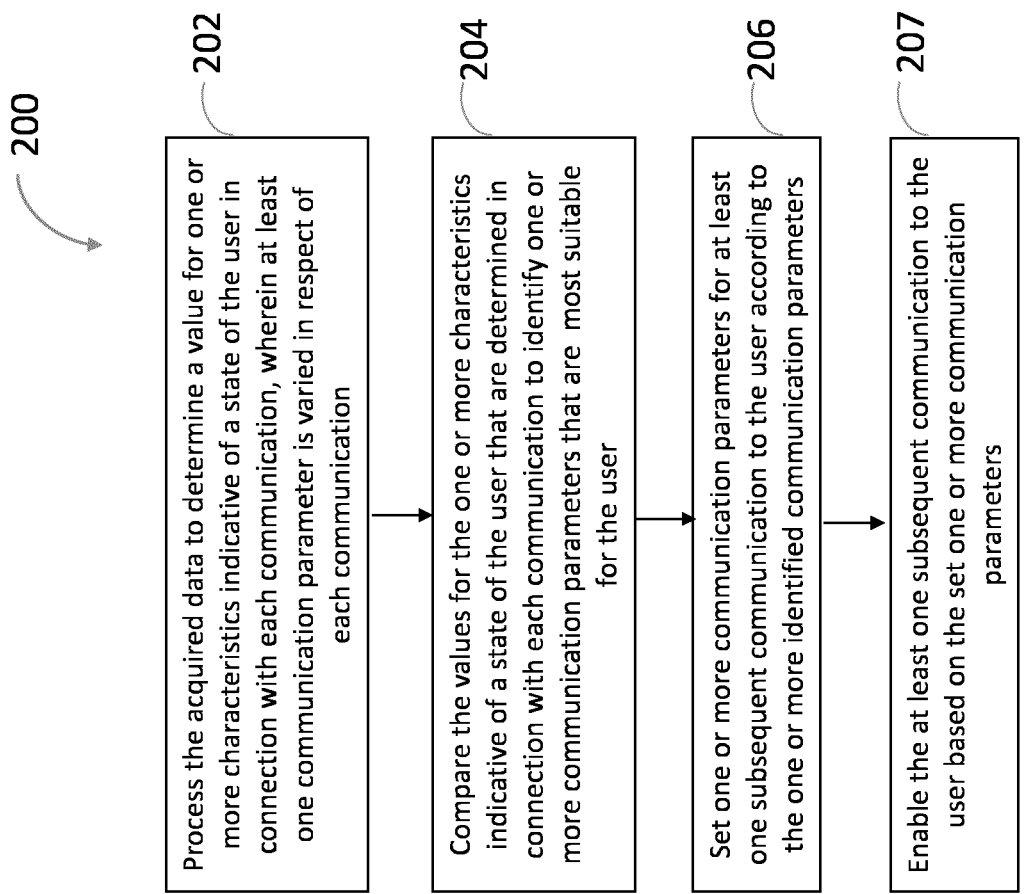
FIG. 2B is a flow chart illustrating a method according to an embodiment.

FIG. 2B shows analogous steps as FIG. 2A, with the addition of the step block 207 depicting the enabling of the at least one subsequent communication to the user based on the set one or more communication parameters.

Analogously to what has been mentioned above, block 206 of FIG. 2B, one or more communication parameters are set for at least one subsequent communication to the user according to the one or more identified communication parameters. The one or more communication parameters that are set for at least one subsequent communication may comprise any one or more of a time for the communication to the user, a duration of the communication to the user, a content for the communication to the user, an affective (for example, emotional) level for the content of the communication to the user, a difficulty level for the content of the communication to the user, a cognitive level for the content of the communication to the user, a form of the communication to the user (for example, the form of the communication may be changed from one form of communication to another form of communication), or any other communication parameter or combination of communication parameters. In some embodiments, the communication parameter set for at least one subsequent communication can include assignment of a person to perform the at least one subsequent communication. For example, the reaction of the user to different people performing the plurality of communications may be analysed to find the best match of person for the user to perform the at least one subsequent communication (which may depend on the availability of the person to perform the at least one subsequent communication).

At block 207 of FIG. 2B, the determined one or more communication parameters set for at least one subsequent communication, trigger, activate, perform, imitate, generate, engender or otherwise enable said at least one subsequent communication. Such can be done via a signal generated and subsequently send to and received by a communication device, for example via a receiving unit of such communication device, such as either automatically change one or more communication parameters of said communication device for the subsequent communication in accordance with the determined one or more communication parameters, or to enable a change of one or more communication parameters of said communication device for the subsequent communication in accordance with the determined one or more communication parameters.

A communication device of the kind mentioned above can be, for example a computer, a tablet, a phone, an mobile phone, a wearable device (e.g. a watch) or any other means configured to communication information between two or more individuals or persons, such as for instance a first person (for example, a healthcare provider, a healthcare specialist, a care giver, a guardian, or any other person) and a second person (e.g. a patient, a user, a subject).

As mentioned earlier, the at least one communication parameters may comprise any one or more of: a time for the communication to the user, a duration of the communication to the user, a content for the communication to the user, an affective (for example, emotional) level for the content of the communication to the user, a difficulty level for the content of the communication to the user, a cognitive level for the content of the communication to the user, a form of the communication to the user, or any other communication parameter or combination of communication parameters.

Additionally or alternatively, an alarm, a notice or notification can be sent to the person that is to perform the at least one subsequent communication (for example, a healthcare provider, a healthcare specialist, a care giver, or any other person) such that they initiate the subsequent communication in accordance with said communication parameter, for instance via an interface, such as the user interface 106, where said subsequent communication can comprise an audio call, a video call, an audio and video call, an e-mail, or any other form of communication or combination of forms of communication In an embodiment in which the one or more communication parameters are adapted based on an identified current activity of the user, it may be inconvenient for the user to receive a communication during the identified activity. In this embodiment, the one or more communication parameters set for the at least one subsequent communication may be adapted based on an identified current activity of the user by adjusting a scheduled time for the at least one subsequent communication to another (for example, more convenient) time. For example, the scheduled time may be adjusted to a time at which the identified current activity is expected to be over. In an example in which the user is out of the house, a time for the at least one subsequent communication may be changed. For example, this may involve delaying the communication until it is detected that the user has returned home via a sensor or a user input. The user may be notified via at least one user interface 106 if they have missed a communication.

In some embodiments, the identified current activity may be tracked and a notification (such as an alert, flag or any other notification) provided when the identified current activity has ended and an appropriate time for the at least one subsequent communication is available. This may be performed automatically by the control unit 102 of the apparatus or may involve user input (for example, from the user or another person). In some embodiments, the person that is to perform the at least one subsequent communication (for example, a healthcare provider, a healthcare specialist, a care giver, or any other person) may be informed that the user is not available at the original time.

In an embodiment in which the one or more communication parameters are adapted based on an identified activity pattern of the user, the activity pattern may be learnt over time. In such an embodiment, one or more communication parameters may be adapted by adjusting a communication schedule for the at least one subsequent communication to fall in the optimal (or most suitable or convenient) moments in time for the user. In some embodiments, the activity pattern of a plurality user may be taken into account to optimise the one or more communication parameters for at least one subsequent communication over the plurality of users.

In an embodiment in which the one or more communication parameters are adapted based on a deviation from an identified activity pattern of the user, one or more communication parameters are adapted such that the at least one subsequent call is expedited or scheduled earlier. For example, the deviation from the identified activity pattern of the user may signal a cause for concern (such as the user sleeping longer compared to the identified activity pattern, a user spending longer at the toilet or in the bathroom compared to the identified activity pattern, or similar). In another example, the deviation from the identified activity pattern of the user may signal that the communication will be inconvenient (for example, the user may have visitors) and the one or more communication parameters may be adapted such that the at least one subsequent call is scheduled as optional or delayed until a later time.

In an embodiment in which the one or more communication parameters are adapted based on an input received from the user indicative of a current state of the user, the user input may be an indication that a subsequent communication will be inconvenient or convenient. For example, the user input may indicate that they are engaging in an activity (such as on the toilet or having visitors) during which they do not wish to receive a subsequent communication and the one or more communication parameters may be adapted to cancel the at least one subsequent communication or reschedule the at least one subsequent communication for another time.

In respect of any of the embodiments described herein, where a deviation in at least one characteristic indicative of the state of the user is detected, the method described may be repeated to re-set one or more communication parameters for at least one subsequent communication to the user. In other words, the calibration procedure is re-started with a new plurality of communications. In this way, it is possible to learn any changes that occur. This can be useful in situations in which a user exhibits a change in their health (for example, the onset of an illness such as dementia, an injury, a fall, or any other change in health) since these changes will be taken into account through the recalibration.

Alternatively or in addition, where a deviation in at least one characteristic indicative of the state of the user is detected, the method may further comprise acquiring contextual information in connection with each communication (as will be explained in more detail with reference to FIG. 3). The contextual information can be any information suitable to put the one or more characteristics indicative of a state of the user into context.

Figure 3:
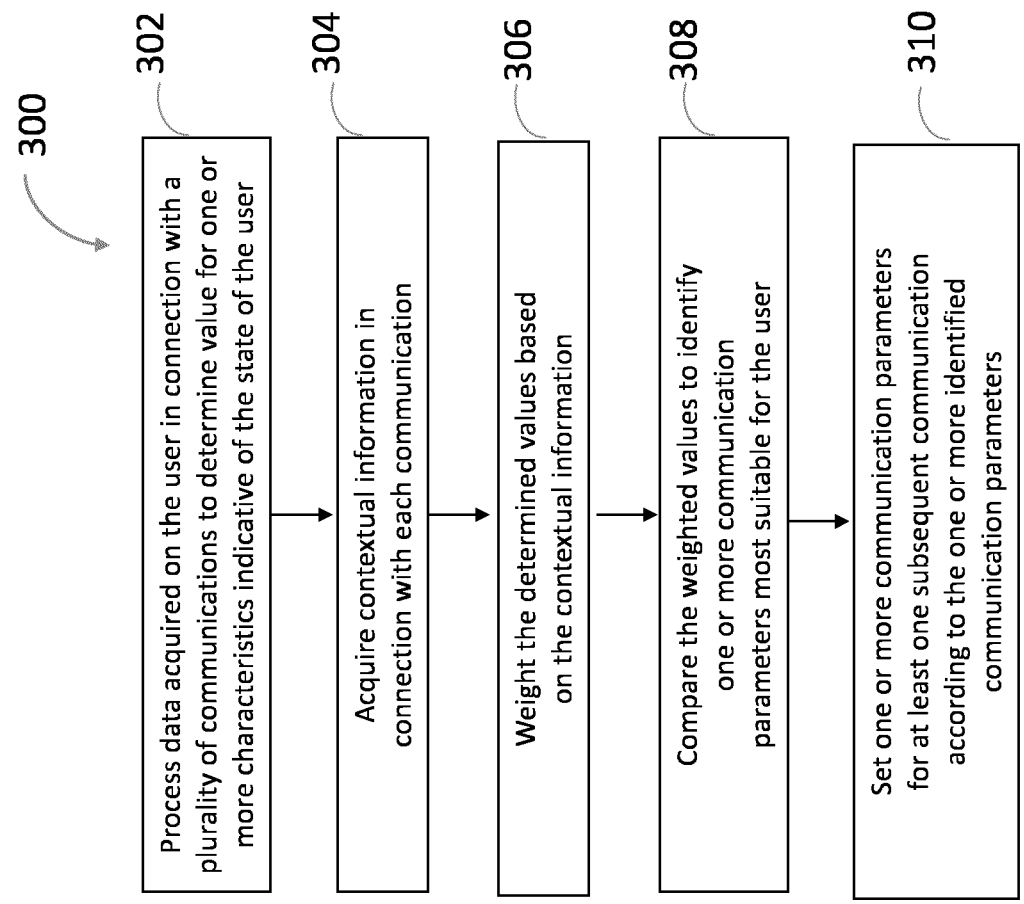
FIG. 3 is a flow chart illustrating a method according to another embodiment.

FIG. 3 illustrates a method 300 for setting one or more communication parameters for at least one communication to a user according to another embodiment. The illustrated method 300 can generally be performed by or under the control of the control unit 102 of the apparatus 100.

With reference to FIG. 3 at block 302, the method described above with respect to block 202 of FIG. 2A is performed and thus the corresponding description will be understood to apply but will not be repeated here. Briefly, a block 302 of FIG. 3, data acquired on the user in connection with a plurality of communications to the user is processed to determine a value for one or more characteristics indicative of a state of the user in connection with each communication. In respect of each of the plurality of communications, at least one communication parameter is varied.

At block 304 of FIG. 3, contextual information in connection with each communication is acquired. The contextual information is any information suitable to put the one or more characteristics indicative of a state of the user into context. The contextual information can comprise real-time data in connection with a communication.

In some embodiments, acquiring contextual information in connection with each communication may comprise controlling at least one sensor in an environment of the user to acquire the contextual information. In other words, the control unit 102 of the apparatus 100 may acquire contextual information from at least one sensor in an environment of the user. Thus, the contextual information may comprise information acquired on the environment in which the user is located. For example, the contextual information can comprise any one or more of a time of day, a light level, an ambient temperature, a $CO_2$ level, a humidity, and a noise level.

Alternatively or in addition, acquiring contextual information in connection with each communication may comprise initiating a communication to the user (or another person such as a healthcare provider, a healthcare specialist, a care giver, or any other person) requesting the contextual information. For example, the control unit 102 of the apparatus 100 may acquire contextual information from one or more user inputs at the one or more user interfaces 106.

At block 306, the determined values for the one or more characteristics indicative of a state of the user are weighted based on the acquired contextual information.

At block 308, the method described above with respect to block 204 of FIG. 2A is performed with the weighted values of the one or more characteristics indicative of a state of the user. Briefly, the weighted values for the one or more characteristics indicative of the state of the user that are determined in connection with each communication are compared to identify one or more communication parameters that are most suitable for the user.

At block 310, the method described above with respect to block 206 of FIG. 2A is performed and thus the corresponding description will be understood to apply but will not be repeated here. Briefly, at block 310 of FIG. 3, one or more communication parameters are set for at least one subsequent communication to the user according to the one or more identified communication parameters.

In some embodiments, the method of FIG. 3 may be performed when a deviation in at least one characteristic indicative of the state of the user is detected. Specifically, prior to block 302, the method may comprise detecting a deviation in at least one characteristic indicative of the state of the user and when the deviation is detected, contextual information may be acquired from the user (at block 302). For example, a deviation in at least one characteristic indicative of the state of the user may trigger sensors to operate outside of the communications in order to acquire additional information that may put the deviation into context. In this way, more accurate data can be collected. In an example, when a deviation is detected, the control unit 102 of the apparatus 100 may collect data (such as audio and video data) continuously for a period of time (for example, for the next 1 day). In this way, more data can be collected.

Alternatively or in addition, the deviation in at least one characteristic indicative of the state of the user may initiate a communication to the user requesting that the user provide contextual information. Alternatively or in addition, the deviation in at least one characteristic indicative of the state of the user may trigger a notification to another person (for example, a healthcare provider, a healthcare specialist, a care giver, or any other person). For example, the notification may instruct the person to ask the user additional questions that relate to obtaining additional context, ask the person to visit the user, or request that the person take any other action that will enable context information to be acquired.

In any of the embodiments described herein, the method described may be performed for a plurality of users. In these embodiments, the method may further comprise assigning a priority value to at least one of the plurality of users. Then, the setting of one or more communication parameters for at least one subsequent communication may take into account the priority value assigned to the at least one of the plurality of users. In some embodiments, the priority value is assigned to the at least one of the plurality of users based on the determined values of the one or more characteristics indicative of the state of the at least one user, a flexibility of the at least one user, or any other information or combination of information indicative of a priority value that may be assigned to the at least one user.

In one example, the user with the highest value for at least one characteristic indicative of the state of the user is prioritised. For example, this user may be allocated a timeslot for subsequent communications that is closest to a preferred timeslot. In another example, a determined optimal period in which to receive a communication can be larger for some users than other users, which can indicate that there is more flexibility to shift at least one subsequent communication for that user to another time slot within the determined optimal period. For some users, multiple optimal periods in which to receive a communication may be identified (for example, the user may prefer communications in the morning or evening, but not in the afternoon). In such an example when a user is not high priority, a large shift in a preferred time slot for that user may be made (for example, from the morning to the evening) instead of only slightly moving the preferred timeslot. Thus, in a multi-user situation, optimal communication settings can be set for communications across multiple users.

In some embodiments, when a deviation in at least one characteristic indicative of the state of the user is detected, the user may be increased to a higher priority level for at least one subsequent communication to that user. The reason for the change in priority level may be rendered to a person that will perform the at least one subsequent communication (for example, a healthcare provider, a healthcare specialist, a care giver, or any other person) to make them aware of the change and optionally any points for attention. For example, the change in priority level may be rendered via one or more user interfaces 106.

In respect of any of the embodiments described herein, where a deviation in at least one characteristic indicative of the state of the user is detected, the method described may be repeated to re-set one or more communication parameters for at least one subsequent communication to the user. In other words, the calibration procedure is re-started with a new plurality of communications. In this way, it is possible to learn any changes that occurred.

In any of the embodiments described herein, the method may comprise further steps that can support machine learning. For example, a database may be provided to store data that is acquired on the user in connection with one or more communications (such as the physiological data, wearable data, audio/visual data, or any other data acquired on the user in connection with one or more communications). The database may be updated after each communication. The database may be part of the memory 110 of the apparatus 100 or may be part of an external memory. An analysis of the data stored in the database can improve the reliability of setting appropriate communication parameters for subsequent communications. In particular, communication parameters set for subsequent communications can become more reliable (or more appropriate for the user) after each communication. In some embodiments, an aggregated learning may also be used by analysing data stored on multiple users.

The stored data can be analysed to determine any features that aid machine learning. For example, the stored data may be analysed to determine the period of time needed to establish reliable predictions of optimal communication parameters (such as optimal scheduled slots) for the user, to determine the features that are most influential to those optimal communication parameters, to determine influencing features via a larger data-set across a plurality of users with similar characteristics (which can reduce the calibration time), to determine long term health trends of the user (such as worsening, stable, improving or the like). The determined features can be useful in understanding the communication parameters that are set for subsequent communications. For example, the long term health of the user can put the urgency of an unscheduled communication into context.

Figure 4:
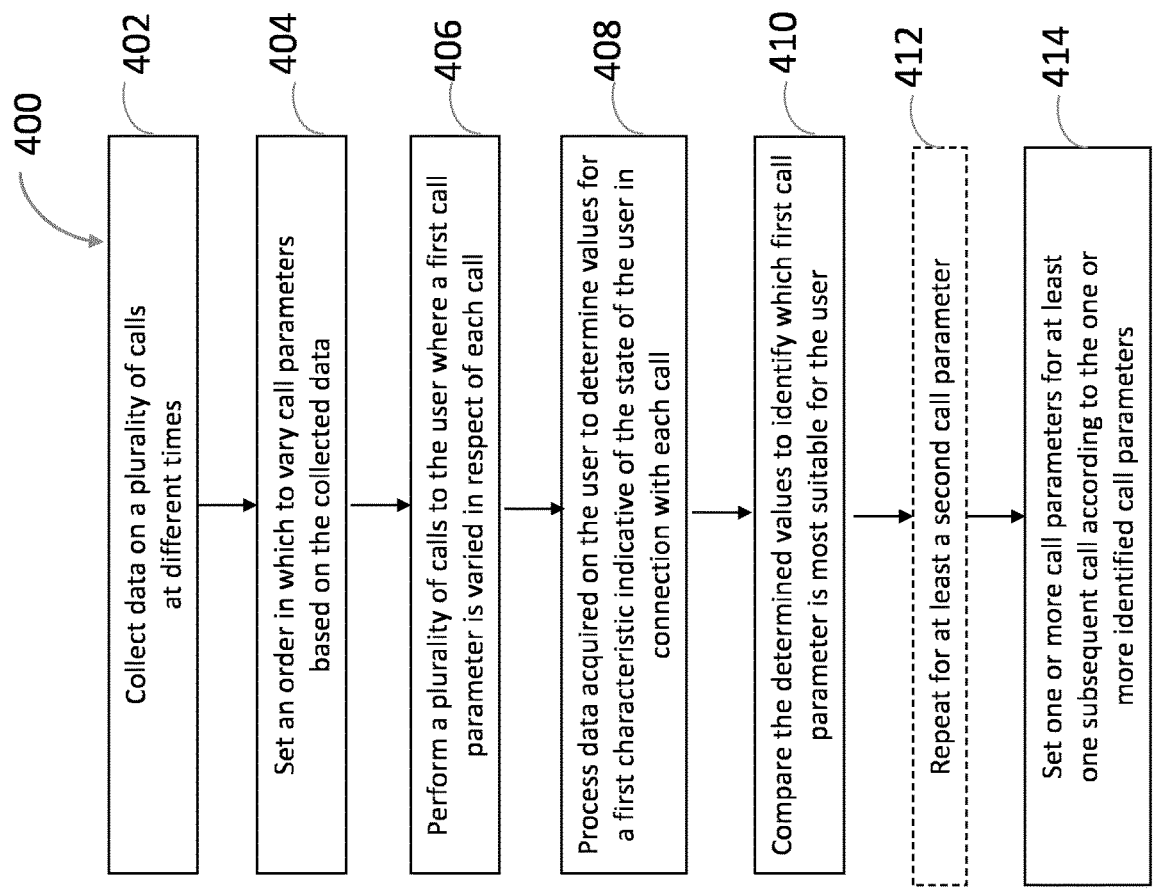
FIG. 4 is a flow chart illustrating a method according to an example embodiment.

FIG. 4 illustrates a method 400 for setting one or more communication parameters for at least one communication to a user according to an example embodiment. The illustrated method 400 can generally be performed by or under the control of the control unit 102 of the apparatus 100.

With reference to FIG. 4 at block 402, data is collected on a plurality of communications at different times. In this example embodiment, the plurality of communications are a plurality of calls. However, it will be understood that this is only an example and the plurality of communications may comprise any other forms of communication or any combination of forms of communication.

In an example of data being collected on a plurality of calls at different times, the data on a plurality of calls at different times may be collected by randomly sampling three weekdays (for example, Monday, Thursday and Friday) to perform three 10 min calls. For example, a time slot may be randomly selected between 10:00-12:00 to make a call on the first day (Monday), a time slot may be randomly selected between 15:00-18:00 on the second day (Thursday) and a time slot may be randomly selected between 18:00-22:00 on the third day (Friday).

At block 404, an order in which to vary call parameters based on the collected data is set. For example, based on the data collected and analysed from the three calls, it may be determined that for this particular user the call parameters are to be calibrated in the following order: 1. Cognitive level, 2. Emotion level, 3. Timing, and 4. Duration.

At block 406, a plurality of calls to the user are performed where a first call parameter is varied in respect of each call. In this example embodiment, the first parameter is the cognitive level. Thus, calls with varying cognitive levels are performed.

At block 408, data acquired on the user is processed to determine values for a first characteristic indicative of the state of the user in connection with each call. The randomness of the cognitive level of each call can be adapted based on data acquired on the user in connection with previous calls since with each call more information is available about the user.

At block 410, the determined values are compared to identify which first call parameter is most suitable for the user. For example, the right level of cognitive capacity that the user is able to comfortably follow and understand can be identified. Once a satisfactory predictability is achieved (for example, once the cognitive skills of the user are estimated with high confidence), the method may proceed straight to block 414 to set one or more call parameters for at least one subsequent call or may proceed to block 412 to first analyse the next calibration parameter.

Thus, optionally, at block 412, the method of blocks 406 and 408 are repeated at least a second call parameter. In this example embodiment, the second parameter is the emotion level. Thus, calls with varying emotion levels are performed. For example, the emotional content of the questions included in the call may be varied in the same manner described above in respect of the cognitive level. In the same way, the method of blocks 406 and 408 may be repeated for the other call parameters of timing and duration. In this way, call parameters that may affect the call quality and the information gathered during the call can be calibrated in an order that is most suitable to the user.

At block 414, the method described above with respect to block 206 of FIG. 2A is performed and thus the corresponding description will be understood to apply but will not be repeated here. Briefly, at block 414, one or more call parameters are set for at least one subsequent call to the user according to the one or more identified call parameters. For example, one or more call parameters are set for at least one subsequent call to the user according to the identified first call parameter, the identified second call parameter and the identified third call parameter.

In an alternative embodiment, instead of the ordered approach described above, a weighted approach may be used where multiple variables are changed simultaneously but are assigned different weights. For example, using a weighted approach in the example embodiment of FIG. 4, the cognitive level will be weighted highest, whereas the duration is weighted lowest. This approach may be useful since not all call parameters may be independent with each other. A weighted approach may increase the speed of processing to arrive more quickly at setting the one or more call parameters for the at least one subsequently call.

According to another aspect, there is also provided a computer program product comprising a computer readable medium, the computer readable medium having computer readable code embodied therein. The computer readable code is configured such that, on execution by a suitable computer or processor, the computer or processor is caused to perform the method or methods described herein.

Aspects of the invention may be implemented in a computer program product, which may be a collection of computer program instructions stored on a computer readable storage device, which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the control unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller. While the invention has been illustrated and described in detail in the drawings and foregoing description, such illustration and description are to be considered illustrative or exemplary and not restrictive; the invention is not limited to the disclosed embodiments.

As described above, there is provided an improved method and apparatus for setting one or more communication parameters for at least one communication to a user. According to the method and apparatus provided, the most appropriate settings for the user can be selected automatically. By learning about the user in certain situations according to the method and apparatus disclosed herein, it is possible to provide smarter communication management and planning. The method and apparatus can be employed in many settings, including monitoring a user at home or at any other location. This can be particularly useful in monitoring elderly users and those users that are unhealthy or unwell. The method and apparatus can also be particularly useful in applications where there are many users and only few professionals initiating communications.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for tailoring at least one subsequent communication to a user, the computer-implemented method comprising:

processing data acquired on the user in connection with a plurality of communications to the user to determine a value for one or more characteristics indicative of a state of the user in connection with each communication, wherein at least one communication parameter is randomized at a first level of randomness in respect of each communication within a first subset of communications of the plurality of communications, and the at least one communication parameter is randomized at a second level of randomness in respect of each communication within a second subset of communications of the plurality of communications, the first and second levels of randomness being different;

comparing the values for the one or more characteristics indicative of the state of the user that are determined in connection with each communication to identify one or more communication parameters that are most suitable for the user;

setting one or more communication parameters for the at least one subsequent communication to the user according to the one or more identified communication parameters; and transmitting, by a communications interface, a signal to a communication device to initiate the at least one subsequent communication, the signal configured to change or enable a change of one or more communication parameters of the communication device for the at least one subsequent communication based on the set one or more communication parameters, wherein the one or more communication parameters of the communication device comprise any one or more of: a time for the at least one subsequent communication to the user, a duration for the at least one subsequent communication to the user, a content for the at least one subsequent communication to the user, an affective level for the content of the at least one subsequent communication to the user, a difficulty level for the content of the at least one subsequent communication to the user, a cognitive level for the content of the at least one subsequent communication to the user, and a form of the at least one subsequent communication to the user.

2. The computer-implemented method as claimed in claim 1, wherein a plurality of communication parameters are randomized in respect of each communication and the plurality of communication parameters are randomized simultaneously or in a predefined order.

3. The computer-implemented method as claimed in claim 1, wherein the data acquired on the user comprises any one or more of: physiological data, psychological data, audio data, visual data, and user input data.

4. The computer-implemented method as claimed in claim 1, the computer-implemented method further comprising:
acquiring contextual information in connection with each communication; and
weighting the determined values for the one or more characteristics indicative of the state of the user based on the acquired contextual information.

5. The computer-implemented method as claimed in claim 4, wherein the contextual information is acquired from at least one sensor in an environment of the user.

6. The computer-implemented method as claimed in claim 1, the computer-implemented method further comprising:
detecting a deviation in at least one characteristic indicative of the state of the user; and
acquiring contextual information from the user when the deviation is detected.

7. The computer-implemented method as claimed in claim 1, the computer-implemented method further comprising:
updating the one or more communication parameters set for the at least one subsequent communication based on any one or more of:
an identified current activity of the user;
an identified activity pattern of the user;
a deviation from an identified activity pattern of the user; and
an input received from the user indicative of a current state of the user.

8. The computer-implemented method as claimed in claim 1, wherein the at least one communication parameter comprises any one or more of:
a time for the communication to the user;
a duration of the communication to the user;
a content for the communication to the user;
an affective level for the content of the communication to the user;
a difficulty level for the content of the communication to the user;
a cognitive level for the content of the communication to the user; and
a form of the communication to the user.

9. The computer-implemented method as claimed in claim 1, wherein the one or more characteristics indicative of the state of the user comprise any one or more of:
a characteristic indicative of an affective state of the user;
a characteristic indicative of a mobility capability of the user;
a characteristic indicative of a level of pain experienced by the user;
a characteristic indicative of a physiological state of the user;
a characteristic indicative of a psychological state of the user;
a characteristic indicate of a strength of the user;
a characteristic indicative of an impairment of the user;
a characteristic indicative of a cognitive ability of the user; and
a characteristic indicative of a level of social skills of the user.

10. The computer-implemented method as claimed in claim 1, the computer-implemented method further comprising:
performing the computer-implemented method for a plurality of users; and
assigning a priority value to at least one of the plurality of users;
wherein setting one or more communication parameters for at least one subsequent communication takes into account the priority value assigned to the at least one of the plurality of users.

11. The computer-implemented method as claimed in claim 1, the computer-implemented method further comprising:
detecting a deviation in at least one characteristic indicative of the state of the user; and
repeating the computer-implemented method to re-set one or more communication parameters for at least one subsequent communication to the user.

12. A computer program product comprising a computer readable medium, the computer readable medium having computer readable code embodied therein, the computer readable code being configured such that, on execution by a suitable computer or processor, the computer or processor is caused to perform the computer-implemented method of claim 1.

13. An apparatus for tailoring one or more subsequent communications to a user, the apparatus comprising:
one or more processors configured to:
process data acquired on the user in connection with a plurality of communications to the user to determine a value for one or more characteristics indicative of a state of the user in connection with each communication, wherein at least one communication parameter is randomized at a first level of randomness in respect of each communication within a first subset of communications of the plurality of communications, and the at least one communication parameter is randomized at a second level of randomness in respect of each communication within a second subset of communications of the plurality of communications, the first and second levels of randomness being different;
compare the values for the one or more characteristics indicative of the state of the user that are determined in connection with each communication to identify one or more communication parameters that are most suitable for the user; and
set one or more communication parameters for the at least one subsequent communication to the user according to the one or more identified communication parameters; and
a communications interface configured to transmit a signal to a communication device to initiate the at least one subsequent communication, the signal configured to change or enable a change of one or more communication parameters of the communication device for the at least one subsequent communication based on the set one or more communication parameters, wherein the one or more communication parameters of the communication device comprise any one or more of: a time for the at least one subsequent communication to the user, a duration for the at least one subsequent communication to the user, a content for the at least one subsequent communication to the user, an affective level for the content of the at least one subsequent communication to the user, a difficulty level for the content of the at least one subsequent communication to the user, a cognitive level for the content of the at least one subsequent communication to the user, and a form of the at least one subsequent communication to the user.

14. An apparatus as claimed in claim 13, the apparatus further comprising:
a memory configured to store the values for the one or more characteristics indicative of the state of the user that are determined in connection with the communications and the associated communication parameters for the communications.

15. An apparatus as claimed in claim 13, wherein the one or more processors is configured to acquire contextual information in connection with the plurality of communications from at least one sensor in an environment of the user.

16. A system for tailoring at least one subsequent communication to a user, the system comprising:
one or more sensors for acquiring data on the user in connection with a plurality of communications, wherein the data acquired on the user comprises any one or more of: physiological data, psychological data, audio data, visual data, and user input;
one or more processors configured to:
process data acquired from the one or more sensors to determine a value for one or more characteristics indicative of a state of the user in connection with each communication, wherein at least one communication parameter is randomized at a first level of randomness in respect of each communication within a first subset of communications of the plurality of communications, and the at least one communication parameter is randomized at a second level of randomness in respect of each communication within a second subset of communications of the plurality of communications, the first and second levels of randomness being different;
compare the values for the one or more characteristics indicative of the state of the user that are determined in connection with each communication to identify one or more communication parameters that are most suitable for the user; and
set one or more communication parameters for the at least one subsequent communication to the user according to the one or more identified communication parameters; and
a communications interface configured to transmit a signal to a communication device to initiate the at least one subsequent communication, the signal configured to change or enable a change of one or more communication parameters of the communication device for the at least one subsequent communication based on the set one or more communication parameters, wherein the one or more communication parameters of the communication device comprise any one or more of: a time for the at least one subsequent communication to the user, a duration for the at least one subsequent communication to the user, a content for the at least one subsequent communication to the user, an affective level for the content of the at least one subsequent communication to the user, a difficulty level for the content of the at least one subsequent communication to the user, a cognitive level for the content of the at least one subsequent communication to the user, and a form of the at least one subsequent communication to the user.

* * * * *